United States Patent [19]

Clark, Jr. et al.

[11] Patent Number: 4,944,185

[45] Date of Patent: Jul. 31, 1990

[54] SYSTEM AND METHOD FOR QUALITATIVELY AND NONDESTRUCTIVELY INSPECTING ADHESIVE JOINTS AND OTHER MATERIALS

[75] Inventors: William G. Clark, Jr., Murrysville; Warren R. Junker, Monroeville, both of Pa.

[73] Assignee: Westinghouse Electric Corp., Pittsburgh, Pa.

[21] Appl. No.: 298,597

[22] Filed: Jan. 17, 1989

[51] Int. Cl.$^5$ ............................................. G01N 29/00
[52] U.S. Cl. ...................................... 73/579; 324/214; 324/226
[58] Field of Search ................... 73/53, 573, 582, 588, 73/643, 614, 657, 579; 324/56, 214, 226, 237

[56] References Cited

U.S. PATENT DOCUMENTS

| | | | |
|---|---|---|---|
| 2,499,466 | 3/1950 | DeForest et al. | 324/456 |
| 3,351,760 | 11/1967 | Brown | 250/303 |
| 4,131,064 | 12/1978 | Ryan | 102/1 R |
| 4,237,766 | 9/1981 | Ensminger | 84/377 |
| 4,346,602 | 8/1982 | Gould et al. | 73/842 |
| 4,391,662 | 7/1983 | Mauthe | 156/64 |
| 4,413,510 | 11/1983 | McCusker et al. | 73/150 A |
| 4,448,525 | 5/1984 | Mikoshiba et al. | 73/643 |
| 4,494,410 | 1/1985 | Van Bochove et al. | 73/644 |
| 4,620,145 | 10/1986 | Dietz et al. | 324/54 |
| 4,641,527 | 2/1987 | Hiroi et al. | 73/582 |

FOREIGN PATENT DOCUMENTS

| | | |
|---|---|---|
| 552920 | 10/1980 | Japan . |
| 142253 | 8/1983 | Japan . |
| 160751 | 9/1984 | Japan . |
| 288377 | 1/1971 | U.S.S.R. . |
| 570833 | 8/1977 | U.S.S.R. . |
| 602852 | 4/1978 | U.S.S.R. . |
| 763767 | 12/1978 | U.S.S.R. . |
| 873108 | 10/1981 | U.S.S.R. . |

OTHER PUBLICATIONS

Publication-NDT International, Jun. 1982, pp. 137-142, "Principles of an Acoustic Impedance Method for Detection and Location of Non-Bonds in Adhesive-Bonded Multi-Layered Joints".
Co-Pending Application Ser. No. 012,775 filed Mar. 16, 1987, by Clark and Junker.

Primary Examiner—Hezron E. Williams
Assistant Examiner—Mark A. Spector

[57] ABSTRACT

A system and method for nondestructively inspecting and monitoring materials that indicates the structural integrity of the material is disclosed. The inspection method includes the following steps. First, the material to be subsequently monitored, is tagged by dispersing a small amount of finely divided particles throughout the material. The tagged material is then applied in accordance with its application, such as adhesive material to two pieces to be joined to form an adhesive joint. When the adhesive joint or other material is to be inspected, the tagged particles are activated to cause an inherent structural resonance in the tagged material. The activation and structural resonance of the material is then monitored and measured with a probe. Finally, the structure resonance of the material is related to the structural integrity of the adhesive joint, the matrix-reinforcement interface integrity of a composite material, or the state of cure of a resin. The tagged particles may be ferromagnetic particles and the probe either an electromagnetic field coil and an actuator or an electromagnetic field coil and an acoustic emission probe. The tagged particles may be piezoelectric particles and the probe either an electric field and an acelerometer or an electric field and an acoustic emission probe. Alternately, the tagged particles may be acoustic impedance mismatch particles and the probe is an ultrasonic inspection probe.

33 Claims, 6 Drawing Sheets

FIG. 1B
(PRIOR ART)
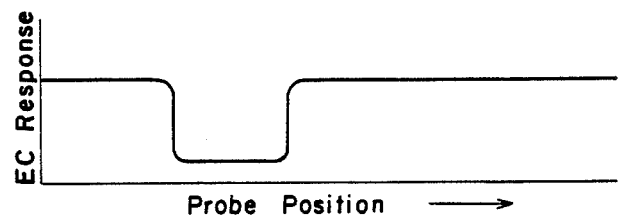
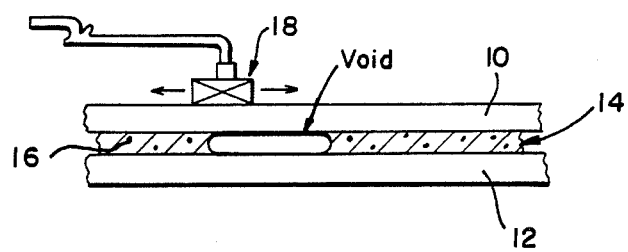
FIG. 1A
(PRIOR ART)

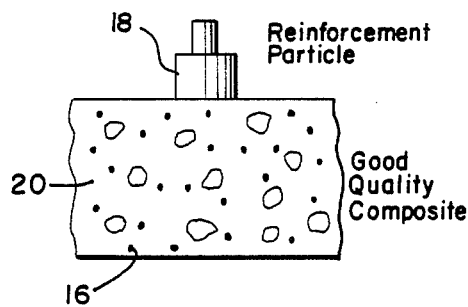
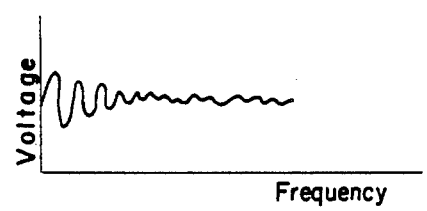
FIG. 3A                FIG. 3D
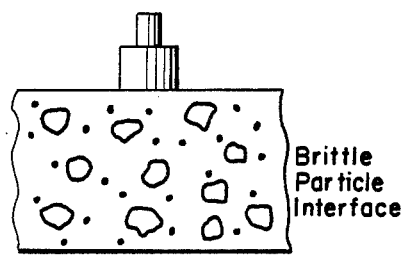
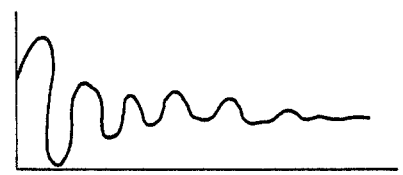
FIG. 3B                FIG. 3E
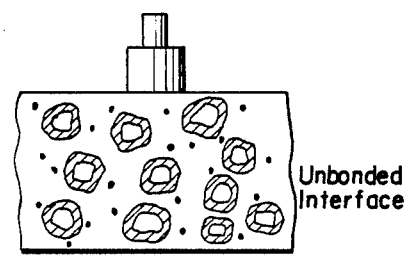
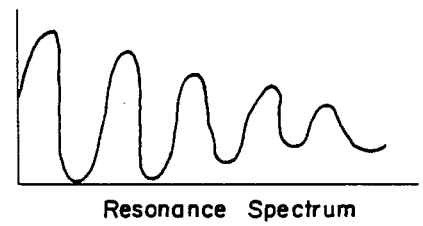
FIG. 3C                FIG. 3F

SYSTEM AND METHOD FOR QUALITATIVELY AND NONDESTRUCTIVELY INSPECTING ADHESIVE JOINTS AND OTHER MATERIALS

TECHNICAL FIELD

The present invention relates to systems for inspecting adhesive joints, resins, and other materials. More particularly the present invention relates to a system and method for nondestructively and qualitatively monitoring and inspecting the integrity of an adhesive joint or composite material, or the state of cure in a resin.

BACKGROUND OF THE INVENTION

The most significant limitation associated with the expanded use of nonmetallic adhesives for structural applications has been the absence of a reliable method of inspection. None of the conventional nondestructive inspection methods such as radiography, ultrasonics, and eddy current can be used to evaluate the general quality of a nonmetallic adhesive joint. Techniques developed for the evaluation of welded and brazed joints do not easily apply to "glued" construction considerations. For example, an epoxy bond between a rubber seal and a steel plate cannot be qualified by radiography because the epoxy cannot be seen; ultrasonics are unable to transmit high frequency sound waves across the interface; and eddy currents fail because of the non-conductivity of the adhesive bond and rubber. Very complicated thermal conductivity tests which may be used for inspection of an adhesive joint have proven unreliable. The importance of finding reliable ways in which to inspect the joints produced by such non-metallic adhesives was dramatically demonstrated by the loss of thermal heat shield tiles in several of the U.S. space shuttle missions.

One of the most promising developments in this field is smart structure technology. Smart structure technology refers to a material assessment concept including the implantation or attachment of sensors to a material to permit remote monitoring of material condition. Some options include the incorporation of optical or acoustic wave guides (glass or wire strands) in reinforced plastic composite components. Periodic or continuous monitoring of the wave guide response is correlated with material integrity and consequently provides a unique nondestructive test capability. While demonstrated successfully for a number of aerospace structure applications, the wave guide approach is limited by two major problems: (1) only materials near the vicinity of the wave guide can be evaluated and (2) prior knowledge of where to place the wave guide is critical to system success.

In 1984 Westinghouse scientists developed a version of the smart structure concept for the inspection of adhesive joints. In this version of the smart structure concept, a nondestructive method of forming and inspecting an adhesive joint to ensure the presence of adhesive and provide a reliable joint between two joined pieces is disclosed. The method includes tagging a nonmetallic adhesive material to be used for a joint by evenly dispersing a small amount of finely-divided ferromagnetic particles throughout the adhesive material. The tagged adhesive material is applied to the two pieces to form the adhesive joint. A magnetic permeability detector device such as an eddy current probe is passed over the surface of one of the pieces in the area of the joint to scan the joint to detect changes in magnetic permeability in the joint area. The detected magnetic permeability of the scanned joint area is recorded to form a magnetic permeability map of the scanned joint area. The map of the scanned joint area is visually examined for relatively low magnetic permeability locations compared to the remaining portions of the scanned joint area. Low magnetic permeability locations indicate voids in the joint. An alternative method includes soaking the adhesive joint with a ferrofluid dye penetrant and passing a magnetic permeability detector over the surface of one of the pieces in the area of the joint to scan the joint to detect changes in magnetic permeability in the joint area. The detected magnetic permeability of the scanned joint area is recorded to form a magnetic permeability record of the scanned joint area. Relatively high magnetic permeability locations indicate voids in the joint where the ferrofluid dye has penetrated.

FIGS. 1A and 1B illustrate the basic principle involved in this method. This simple test is used to determine the presence of the adhesive - an absolutely critical bond integrity parameter. Variations in this concept have been proposed for the assessment of a wide variety of materials where the absence or presence of the tagged particles can be used to indicate material integrity. The technique has been explored for the assessment of composite, caulking, and insulation systems as well as powder processing and foam core structures. Although the ferromagnetic tagging concept can provide important information regarding material continuity, the applicants have observed that tagging alone cannot reflect bond strength.

A recent development involving tagging combined with the utilization of an electromagnetic field probe and vibration monitor has led the inventors to a unique nondestructive approach to the qualitative (and perhaps quantitative) assessment of bond integrity in adhesive joints and overall structural integrity in composite materials as explained below.

SUMMARY OF THE INVENTION

It is an object of the present invention to provide a system and method for nondestructively inspecting and monitoring adhesive joints that indicates the structural integrity of the joint.

It is another object of the present invention to provide a system and method for nondestructively inspecting and monitoring composite materials that indicates the matrix-reinforcement interface integrity.

It is another, object of the present invention to provide a system and method for nondestructively inspecting and monitoring the state of cure in resins.

These and other objects are achieved by the inspection system and method of the present invention which includes the following steps. First, the material to be subsequently monitored is tagged by dispersing a small amount of finely divided particles throughout the material. The tagged material is then applied in accordance with its application, such as adhesive material to two pieces to be joined to form an adhesive joint. When the adhesive joint or other material is to be inspected, the tagged particles are activated to cause an inherent structural resonance in the tagged material. The activation and structural resonance of the material is then monitored and measured with a single probe. Finally, the structural resonance of the material is related to the structural integrity of the adhesive joint, the matrix-reinforcement interface integrity of a composite material, or the state of cure of a resin. The tagged particles may be ferromagnetic particles and the probe may include either an electromagnetic field coil and an actuator or an electromagnetic field coil and an acoustic emission probe. The tagged particles may be piezoelectric particles and the probe either an electric field and an accelerometer or an electric field and an acoustic emission probe. Alternately, the tagged particles may be acoustic impedance mismatch particles and the probe is an ultrasonic inspection probe.

Various additional advantages and features of novelty which characterize the invention are further pointed out in the claims that follow. However, for a better understanding of the invention and its advantages, reference should be made to the accompanying drawings and descriptive matter which illustrate and describe preferred embodiments of the invention.

BRIEF DESCRIPTION OF THE DRAWINGS

FIGS. 1A and 1B are illustrations of an eddy current probe detecting a void in an adhesive joint according to a prior art technique, and a graphic illustration of the results of the probe, respectively.

FIGS. 3A-3C schematically illustrate test probes testing various composite materials and FIGS. 3D-3F are graphic illustrations of the resonance spectrum of the probe results of FIGS. 3A-3C, respectively.

DETAILED DESCRIPTION OF PREFERRED EMBODIMENTS

Figure 2A:
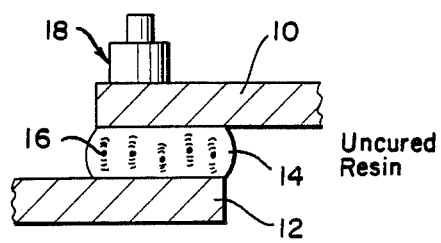
FIGS. 2A-2C schematically illustrate test probes testing uncured resin, cured resin, and an unbonded joint.
Figure 2D:
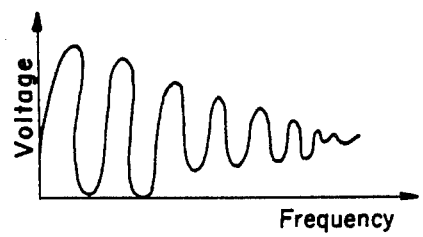
FIGS. 2D-2F are graphic illustrations of the resonance spectrum of the probe results of FIGS. 2A-2C, respectively.
Figure 2B:
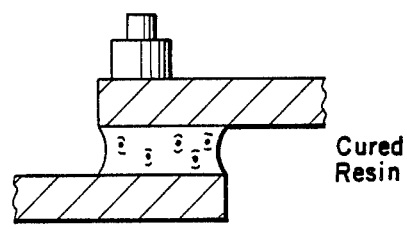
Figure 2E:
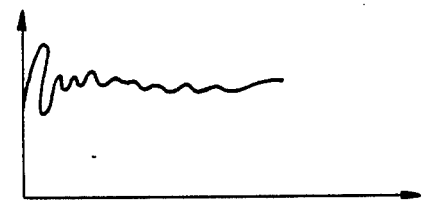
Figure 2C:
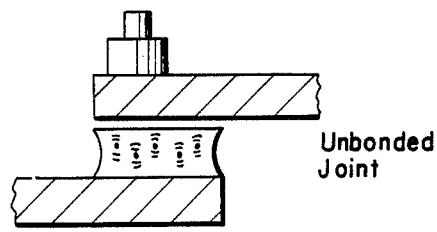
Figure 2F:
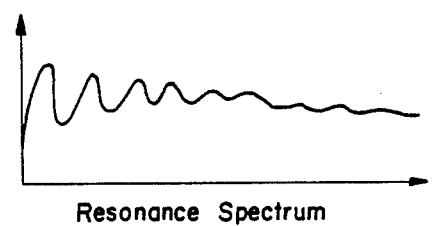

The tagged particle smart structure system and method for qualitatively and nondestructively inspecting a material according to one embodiment of the present invention involves tagging the material with implanted particles and subsequently analyzing the particle vibration signature that corresponds to variations in the condition of the material. Specifically, and referring to FIG. 2, pieces 10 and 12 to be joined are connected by an adhesive material 14 such as an epoxy resin. Tagged particles 16 may be ferromagnetic particles such as iron oxide 16a. When the adhesive joint 14 is to be tested, test probe 18, which serves as both a tagged particle activator as well as a monitor of the particle activation, is passed over piece 10. Test probe 18 need not be one unit with both activation and monitoring capabilities. Test probe 18 may be formed of two separate units, a tagged particle activator and an activation detector. Such activators and monitors are well known as discussed below. The results of the monitoring function of test probe 18 can be graphically illustrated as a resonance spectrum. These results may be produced automatically by a microprocessor/controller, such as an INTEL 80386 based controller such as the AT&T 6386 or the TANDY 4000, using existing software connected to test probe 18. The graph also may be produced manually from data obtained from test probe 18. The resulting graph is visually examined and compared with known resonance signatures for good quality joints.

Where the resin is uncured as in FIG. 2A, the resonance spectrum will have the relative characteristics shown in FIG. 2D. Where the resin is cured as in FIG. 2B, the resonance spectrum will have the relative characteristics shown in FIG. 2E. Where the joint is unbonded as in FIG. 2C, the resonance spectrum will have the relative characteristics shown in FIG. 2F. Thus, by analyzing the resonance spectrum, the state of the joint can be assessed. With an adhesive joint, its structural integrity is assessed. With a resin type material, its state of cure may be assessed. For example, as curing occurs, the resin stiffens. This affects the resonance properties resulting in the relatively large amplitude signatures of FIG. 2D, and the relatively small amplitude signatures of FIGS. 2E and 2F.

It is apparent from FIG. 2 that as the epoxy resin cures and forms a structurally sound joint, the hardened matrix of tagged adhesive 14 restricts the motion of tagged ferromagnetic particles 16. This results in a significant change in the vibration signature of adhesive joint 14. This is because the joint integrity is related to the stiffness or modulus of the joint as indicated by the motion of tagged particles 16. Thus, this system offers a unique approach to resin curve monitoring.

FIG. 3 illustrates the use of the inspection system applied to a metal matrix composite material 20. The particle motion signature reflects the integrity of the matrix-reinforcement interface boundary. FIG. 3A shows a good quality metal matrix composite and this is indicated by the relative resonance spectrum having the characteristics shown in FIG. 3D. FIG. 3B illustrates a brittle particle interface in the metal matrix composite. This condition has a relative resonance spectrum as shown in FIG. 3E. FIG. 3C shows an unbonded interface in the metal matrix composite. The characteristics of the resonance spectrum for this condition are illustrated in FIG. 3F. Thus, the qualitative and nondestructive inspection system of the present invention also works with metal matrix composites, which indicate the strength and bonding between the matrix material and the composite material. A more solid mass such as that of FIG. 3A, has a lower amplitude as shown in FIG. 3D. FIGS. 3E and 3F have larger amplitudes, representative of the relatively weaker bonds and less solid mass of the materials of FIGS. 3B and 3C. A higher amplitude therefore represents a bad composite.

Figure 4B:
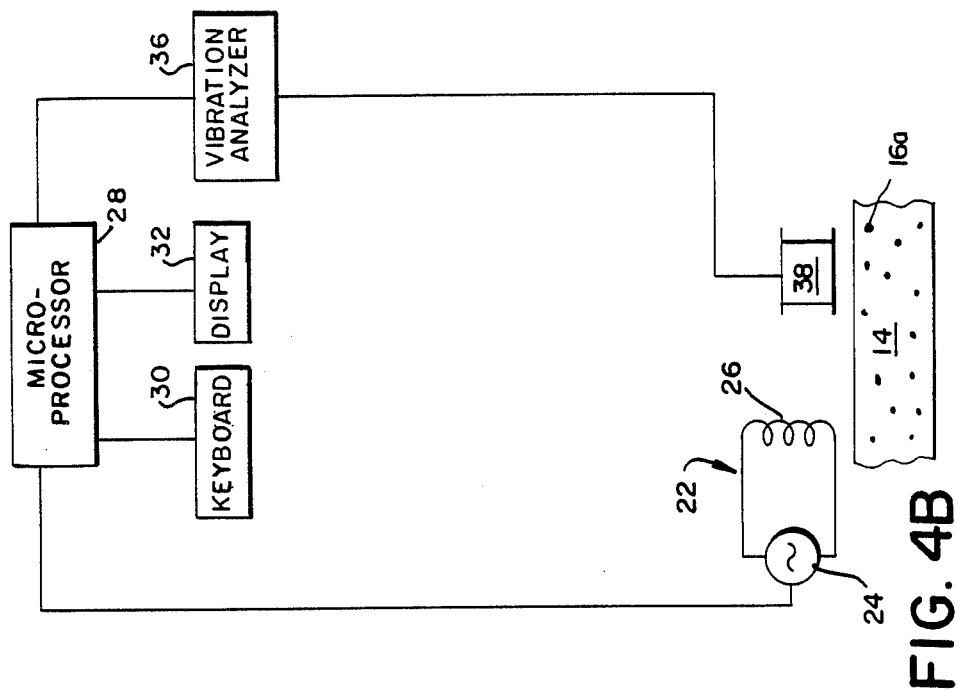
FIGS. 4A and 4B are schematic illustrations of systems used to inspect material using tagged ferromagnetic particles.
Figure 4A:
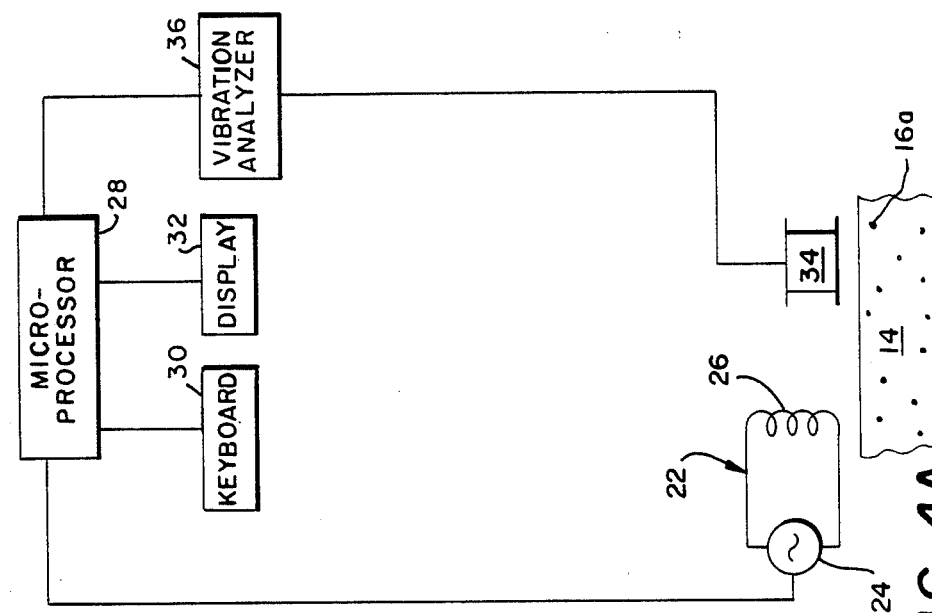

When using ferromagnetic particles as the tagging system, test probe 18 may be an electromagnetic field coil and an accelerometer or an electromagnetic field coil and an acoustic emission probe. Conventional electromagnetic signal generators such as those made by General Radio Instruments may be used. High current, low voltage excitation is preferred. FIG. 4A schematically illustrates a system for analyzing a test material using tagged ferromagnetic particles. In this system the monitor and the activator are shown separately. Tagged particle activator 22 may include electromagnetic generator 24 and energizing coil 26. The activation of tagged particles 16a is controlled by microprocessor/controller 28. Keyboard 30 and display 32 are connected to microprocessor/controller 28 to facilitate the input and output of information. Accelerometer or vibration detector 34 is connected to microprocessor/controller 28 through vibration analyzer 36. Analogous probe components are used whether ferromagnetic, piezoelectric, or impedance mismatch particles are used to tag the material. An appropriate tagged particle activator 22 and vibration detector 34 are used for each application. In FIG. 4B, the detector is an acoustic emission detector 38.

Figure 5B:
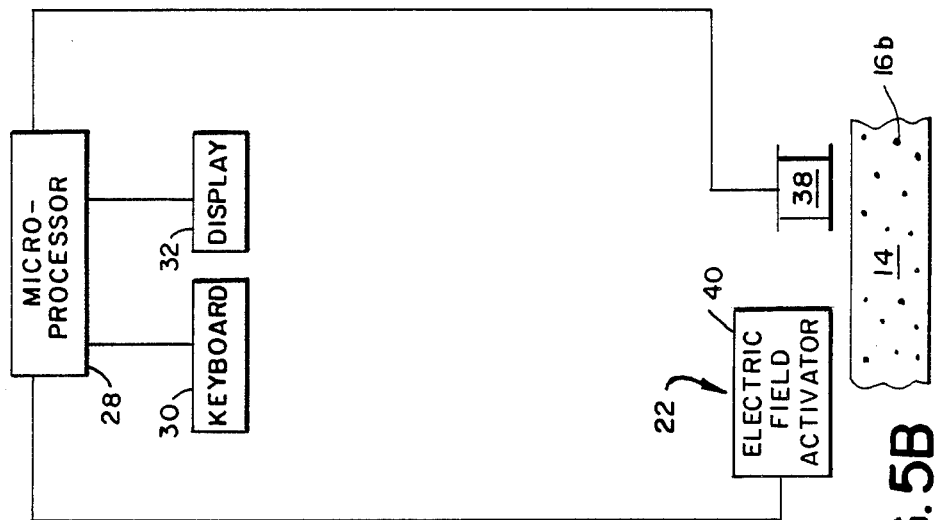
FIGS. 5A and 5B are schematic illustrations of systems used to inspect material using tagged piezoelectric particles.
Figure 5A:
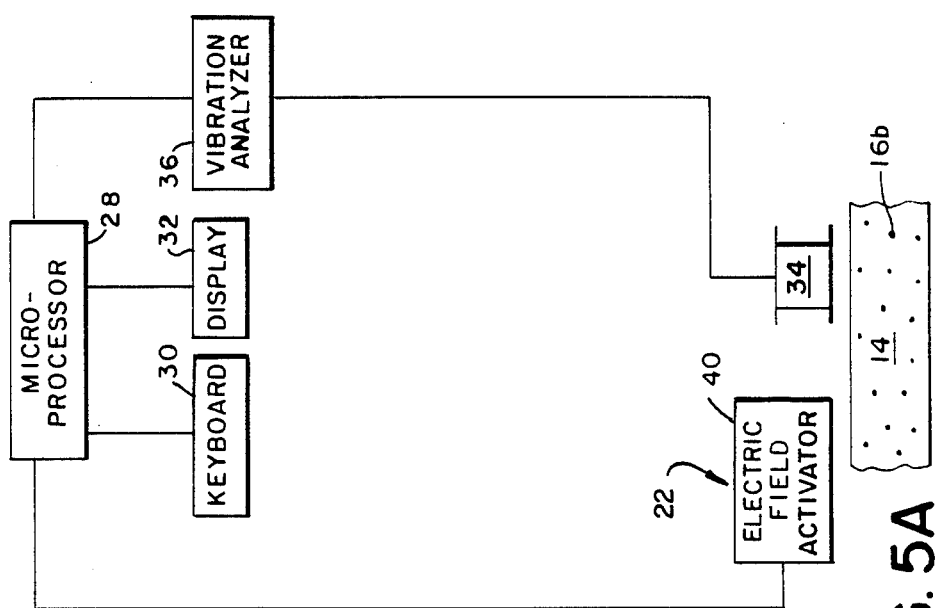

Alternatively, piezoelectric particles such as quartz or barium titanate may be used as tagged particles 16. In this instance, test probe 18 may be either an electric field and accelerometer or an electric field and an acoustic emission probe. The piezoelectric particles vibrate to reflect the material modulus when exposed to the electric field of test probe 18. General Radio Instruments signal generators using low current, high voltage excitation may be used. FIG. 5A shows a system similar to FIG. 4 for piezoelectric tagged particles 16b. Tagged particle activator 22 includes electric field activator 40. The detector is an accelerometer or vibration detector 34. In FIG. 5B, the detector is acoustic emission detector 38.

Figure 6:
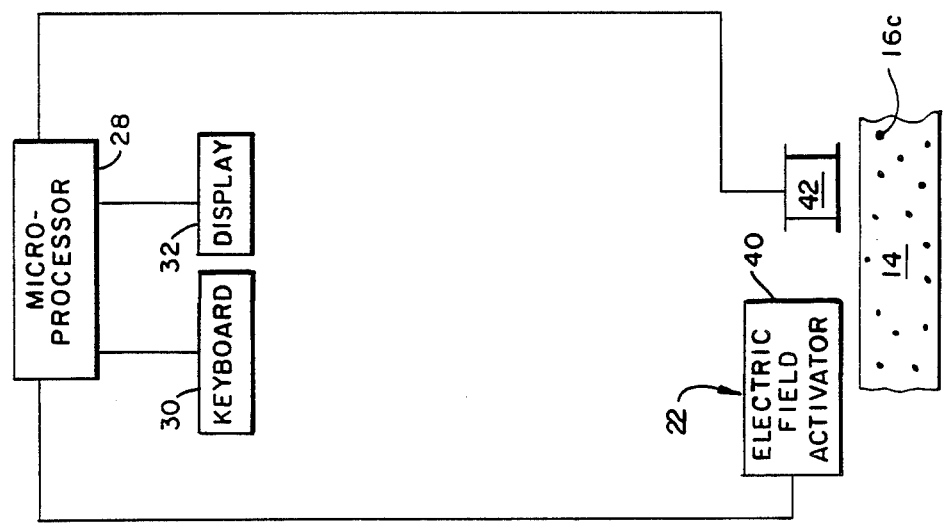
FIG. 6 is a schematic illustration of a system used to inspect material using tagged particles having an acoustic impedance mismatch with the inspected material.

Another alternative is to tag adhesive 14 or other material to be tested with particles 16 that are selected to have a predetermined acoustic impedance mismatch with the adhesive matrix material so that an acoustic spectroscopic analysis would indicate the properties of the adhesive including the state of cure or modulus. FIG. 6 illustrates a similar system in which tagged particles 16c have an acoustic impedance mismatch with the adhesive matrix material. Probe 18 is an ultrasonic inspection probe 42.

The tagged particle smart structure concept described here is a unique enhancement of and improvement over the conventional resonance testing or vibration signature analyses approach to material and component integrity assessment. The tagged particle system goes beyond merely indicating the presence of adhesive or other tested for material. This system indicates the integrity of the material beneath the test probe and is not confused by the vibration characteristics of the component adhesive or metal matrix composite. The tagged particle approach provides a material assessment procedure that is applicable to a wide range of materials and many inspection options, including process interactive NDE (nondestructive evaluation) and in-service performance monitoring of material qualities. A unique advantage associated with the selection of ferromagnetic particles and ferrite (iron oxide) in particular, is the enhanced particle interaction produced by the magnetic field. This feature reduces the particle concentration needed to interrogate the entire material volume. However, the procedure using ferromagnetic tagged particles is applicable only to materials which do not exhibit inherent ferromagnetic properties which would limit the ability to energize and assess tagged particle behavior.

Specific details regarding tagged particle size and concentration, electromagnetic probe frequency and signal analysis capabilities are a function of each particular material system and the properties to be measured. Therefore, optimization of the technique must be established through empirical experimental methods. For example, piezoelectric particles are used in lieu of ferromagnetic particles if ferromagnetic particles are otherwise used in the tested material. Particle size is chosen to minimize the potential impact on the performance of the adhesive or composite material. Additionally, by selecting the particle size and density, the material to be tagged can be custom designed to exhibit certain characteristics. The resonance signature of the material will have predetermined prominent resonance frequencies and amplitudes under certain conditions. Generally, smaller particles have less influence on the inherent properties of the matrix. Particle size must also be considered in conjunction with particle loading or particle density. It is envisioned that particle loading should range between 1% and 10% by weight and that the particle sizes should be on the order of 100A to 500A.

The ability to detect resonant frequency shifts, changes in vibration amplitude, or changes in damping characteristics—which correlate with bond strength or composite performance—defines sensitivity options. State of the art vibration monitors, such as manufactured by Gould Inc., and acoustic emission instruments such as manufactured by Physical Acoustics Corp. are capable of vibration signal analyses far greater than previously thought necessary for material performance assessments.

The systems illustrated in FIGS. 4-6 interpret the resonance phenomenon preferably by evaluating a plurality of parameters such as the phase and amplitude of resonance. Thus, the data analysis software used with the microprocessor should include two dimensional pattern recognition. The software package should also permit the creation of a learning algorithm to expedite system usage.

In instances where the slight inducement of ferromagnetic properties to a normally nonmagnetic material might pose an application problem, ferromagnetic particles with a Curie point below the intended operating temperature could be used. Testing for material integrity would be conducted at a temperature below the Curie point of the tagged particles.

With regard to specific applications for the active particle tagging concept discussed above, a number of possible options are summarized below. Virtually any advanced metal matrix composite material can be tagged by active particles to enhance inspectability. Material systems without ferromagnetic components can be tagged with ferrite particles. Magnetic composites can be evaluated with piezoelectric tagging.

Ferromagnetic or piezoelectric particle tagged polymeric adhesives can be used to join polymers, metals, or ceramics to each other. Virtually any one or two part thermosetting or thermoplastic adhesive or glue can be modified by tagging to permit the assessment of bond quality.

Bonding tapes used to join plastic sheets or pipes can be tagged to permit joint assessment in a manner similar to adhesives.

Ferromagnetic particles can be blended with concrete and cement formulations to create a smart material with resonance properties that correspond to structural integrity.

Asphalt paving materials can be tagged like cement to permit the easy assessment of material condition and ultimately, service induced degradation.

Piezoelectric or ferromagnetic particles can be used to tag epoxy resin based materials including composites to provide a method of cure monitoring.

Active particle tagging of structural ceramic materials including aluminum oxide, silicon carbide, etc., can provide a convenient and rapid method of material assessment.

Ceramic and plastic biomedical implants can be tagged with ferromagnetic particles which would permit the in-place assessment of serviceability.

Foam core laminar composites can be tagged to provide a convenient method of material assessment applicable to in-service conditions. Degradation of the foam core (metallic, ceramic, or plastic) can easily be monitored through changes in resonance properties.

Diagnostic coatings based on active particle tagging can be used on existing structures to provide a method of monitoring the near surface integrity of the underlying material. For example, spraying concrete structures with a ferrite tagged epoxy coating and then energizing the coating with an electromagnetic field may reflect the condition of the underlying concrete.

Active particle tagged composite materials of all kinds provide a relatively low cost "smart skin" option where remote scanning with the appropriate sensor can reveal material integrity.

Flexible seals, gaskets, and O-rings can be tagged to permit the remote assessment of presence and activation; a compressed O-ring would give a different signal than a non-compressed ring.

Tagging options also are being considered for process control concepts where active particle tagging is used in an interactive mode to monitor and control the process. For example, the powder blending processes critical to the manufacture of fuel pellets, metal matrix composites, etc., could be monitored and controlled by tagging the powder so that the mixture could be qualified before moving on to further processing. Once tagged, the change in signature with processing condition could further serve to assess the material and process control.

We claim:

1. A method for nondestructively monitoring the structural integrity of a material wherein the material is impregnated with tagged particles, said system comprising the steps of:
   activating said tagged particles to cause an inherent structural resonance in the material;
   monitoring and measuring the activation and structural resonance of said material; and
   relating the structural resonance of said material to the structural integrity of the material.

2. A method according to claim 1 wherein said material comprises adhesive.

3. A method according to claim 2 wherein said adhesive comprises epoxy.

4. A method according to claim 1 wherein said material comprises a resin and the structural resonance of said resin is related to the state of cure of said resin.

5. A method according to claim 1 wherein said material comprises a composite material and the structural resonance of said composite material is related to the integrity of the matrix reinforcement interface boundary of said composite material.

6. A method according to claim 1 wherein said tagged particles comprise ferromagnetic particles.

7. A method according to claim 6 wherein said tagged ferromagnetic particles comprise iron oxide.

8. A method according to claim 6 wherein said tagged ferromagnetic particles have a Curie point below the intended operating temperature of the adhesive joint and said activating step is performed at a temperature below the Curie point of the tagged ferromagnetic particles.

9. A method according to claim 6 wherein said tagged ferromagnetic particles are activated with high current, low voltage conditions.

10. A method according to claim 6 wherein said monitoring and measuring steps are performed with a probe comprising an electromagnetic field coil and an accelerometer.

11. A method according to claim 6 wherein said monitoring and measuring steps are performed with a probe comprising an electromagnetic field coil and an acoustic emission detector.

12. A method according to claim 1 wherein said tagged particles comprise piezoelectric particles.

13. A method according to claim 12 wherein said tagged piezoelectric particles comprise quartz.

14. A method according to claim 12 wherein said tagged piezoelectric particles comprise barium titanate.

15. A method according to claim 12 wherein said tagged piezoelectric particles are activated with low current, high voltage conditions.

16. A method according to claim 12 wherein said monitoring and measuring steps are performed with a probe comprising an electric field activator and an accelerometer.

17. A method according to claim 12 wherein said monitoring and measuring steps are performed with a probe comprising an electric field activator and an acoustic emission detector.

18. A method according to claim 1 wherein said tagged particles comprise acoustic impedance mismatch particles and said monitoring and measuring steps are performed with a probe comprising an ultrasonic inspection probe.

19. A method according to claim 1 wherein the structural resonance is related to the structural integrity by analyzing the particle vibration signature which varies with variations in the condition of the material.

20. A method according to claim 1 wherein said tagged particles have diameters between 100A and 500A.

21. A method according to claim 1 wherein said tagged particles comprise from 1% to 10% by weight of the tagged material.

22. A method for nondestructively monitoring the structural integrity of a material, said method comprising the steps of:
   tagging the material by dispensing a small amount of finely divided particles throughout the material;
   forming a structure with said tagged material;
   activating said tagged particles to cause an inherent structural resonance in said material;
   monitoring and measuring the activation and structural resonance of said material; and
   relating the structural resonance of said material to the structural integrity of the material.

23. A method according to claim 22 wherein said tagged particles have diameters between 100A and 500A.

24. A method according to claim 22 wherein said tagged particles comprise from 1% to 10% by weight of the tagged material.

25. A system for nondestructively monitoring the structural integrity of a material that has been impregnated with tagged particles, comprising:
   means for activating said tagged particles in order to cause structural resonance in the material, and
   means for monitoring and measuring the activation and structural resonance of the material.

26. A system as defined in claim 25, wherein said means for activating said tagged particles includes an alternating electromagnetic field generator.

27. A system as defined in claim 26, wherein said means for monitoring and measuring said activation and structural resonance includes an accelerometer.

28. A system as defined in claim 26, wherein said means for monitoring and measuring said activation and structural resonance includes an acoustic emission detector.

29. A system as defined in claim 26, wherein said means for activating said tagged particles includes an electric field actuator.

30. A system as defined in claim 29, wherein said means for monitoring and measuring said activation and structural resonance includes an accelerometer.

31. A system as defined in claim 29, wherein said means for monitoring and measuring said activation and structural resonance includes an acoustic emission detector.

32. A system as defined in claim 25, wherein said tagged particles are ferromagnetic particles.

33. A system as defined in claim 25, wherein said tagged particles are piezoelectric particles.

* * * * *